United States Patent [19]

Wu et al.

[11] Patent Number: 5,656,609
[45] Date of Patent: Aug. 12, 1997

[54] METHOD OF ENHANCING AND/OR PROLONGING EXPRESSION OF GENE INTRODUCED INTO A CELL USING COLCHICINE

[75] Inventors: George Y. Wu; Catherine H. Wu, both of Avon, Conn.

[73] Assignee: University of Connecticut, Storrs, Conn.

[21] Appl. No.: 42,870

[22] Filed: Apr. 5, 1993

Related U.S. Application Data

[63] Continuation-in-part of Ser. No. 950,789, Sep. 24, 1992, abandoned.

[51] Int. Cl.$^6$ .................... A01N 37/18; A01N 43/04; A61K 31/16; C12N 15/09
[52] U.S. Cl. .................... 514/44; 435/69.1; 435/172.3; 435/69.2; 514/2; 514/8; 514/629; 536/23.1; 935/34; 935/52; 935/55
[58] Field of Search .................... 514/44, 2, 8, 629; 424/529; 435/172.1, 172.2, 172.3, 69.1, 69.2; 935/26, 34, 52, 55; 536/23.1

[56] References Cited

U.S. PATENT DOCUMENTS 5,166,320  11/1992  Wu et al. .................... 530/395
5,354,844  10/1994  Beug et al. .................... 530/345

FOREIGN PATENT DOCUMENTS

WO 92/05250  4/1992  WIPO.
WO 92/19749  11/1992  WIPO.
WO 92/20316  11/1992  WIPO.
WO 92/22635  12/1992  WIPO.

OTHER PUBLICATIONS

Furlanetto, "Receptor-Mediated Endocytosis and Lysosomal Processing of Insulin-Like Growth Factor I by Mitogenically Responsive Cells" *Endocrinology*, vol. 122, No. 5, pp. 2044-2053, May 1988.

Stryer, *Biochemistry, Third Edition*, 1988, W.H. Freeman and Company, New York, USA, pp. 944-946.

Curiel et al. "Adenovirus enhancement of transferrin-polylysine-mediated gene delivery" PNAS 1991, vol. 88, pp. 8850-8854.

Wu et al. "Receptor-mediated Gene Delivery and Expression in Vivo" Journal of Biological Chemistry 1988, vol. 263, No. 29, pp. 14621-14624.

Zenke et al. "Receptor-mediated endocytosis of transferrin-polycation conjugates: An efficient way to introduce DNA into hematopoietic cells" PNAS 1990, vol. 87, pp. 3655-3659.

Cristiano et al. "Hepatic gene theraphy: Adenovirus enhancement of receptor-mediated gene delivery and expression in primary hepatocycles" PNAS 1993, vol. 90, pp. 2122-2126.

Wu et al. 1989. J. Biol. Chem. 264(29):16985-16987.

Wu et al. Biotherapy 3(1):87-95.

Kaufman et al. 1990 Am J. Physiol. 258(1 pt 1) pp. G129-G137.

*Primary Examiner*—Brian R. Stanton
*Attorney, Agent, or Firm*—Lahive & Cockfield

[57] ABSTRACT

The expression of polynucleotide introduced into a cell by means of a targeted complex of the polynucleotide linked to a cell-specific binding agent can be enhanced and prolonged by inhibiting translocation or fusion of endosomes to lysosomes using colchicine.

12 Claims, 2 Drawing Sheets

METHOD OF ENHANCING AND/OR PROLONGING EXPRESSION OF GENE INTRODUCED INTO A CELL USING COLCHICINE

RELATED APLICATIONS

This application is a continuation-in-part of U.S. patent application Ser. No. 07/950,789 filed Sep. 24, 1992, now abandoned, the contents of which are hereby incorporated by reference.

GOVERNMENT SUPPORT

The work leading to this invention was supported, in part, by research grants from the United States government.

BACKGROUND OF THE INVENTION

The benefits of gene therapy for alleviating or correcting defects in the production of proteins are widely recognized and a number of gene delivery systems have been developed. One method involves using viruses to deliver the exogenous gene to a cell but this method introduces vital genes along with the new gene and undesirable vital effects may be produced.

Another method involves targeting a polynucleotide to a cell in vivo where it is then expressed. This can be accomplished using a soluble complex of two linked components: 1) a polycation, e.g., poly-L-lysine, that can bind a polynucleotide in a strong but non-damaging interaction and 2) a ligand which can be targeted specifically to a cell surface molecule unique to the cell. See Wu, G. Y. and Wu, C. H. (1988) *J. Biol. Chem*, 263:14621–14624. The complex specifically binds the targeted cell and is internalized by endocytosis resulting in the incorporation of the polynucleotide.

During endocytosis, the macromolecule to be ingested is enclosed by a small portion of the plasma membrane which pinches off to form an intracellular vesicle or endosome. Newly synthesized lysosomes from the Golgi apparatus are translocated and fused to endosomes. After fusion, the body is called an endolysosome which then develops into a mature lysosome. Lysosomes contain a wide variety of degradative enzymes and, therefore, material in lysosomes can be broken down.

Although transient gene expression may be desirable for some applications of gene therapy, in many other applications, persistent or enhanced expression of the polynucleotide would be required. There exists a need for a method of introducing DNA into cells in vivo so that expression can be enhanced and made to persist. One method for persistent gene expression is to induce replication of the targeted cell(s) (U.S. patent application Ser. No. 588,013, filed Sep. 25, 1990). Zenke et al. recently reported that chloroquine can be used to raise the pH in the targeted cells' lysosomes during "transferrinfection" thus inhibiting degradation of the exogenous gene within lysosomes and increasing the amount of gene incorporated by the cell. See Zenke, M. et al, (May 1990) *PNAS USA* 87:365–3659. Some investigators have demonstrated that polynucleotide incorporation during transferrinfection can be enhanced by cointernalization of the carrier-polynucleotide complexes with certain viruses. See Curiel et al. (October 1991) *PNAS USA* 88:8850–8854.

SUMMARY OF THE INVENTION

This invention pertains to a method of enhancing the amount of a targeted polynucleotide which is internalized by a cell and of prolonging expression thereof. A soluble molecular complex is used to target a polynucleotide to a specific cell in vivo or in vitro. The amount of the polynucleotide internalized is enhanced and/or prolonged by inhibiting translocation or fusion of endosomes to lysosomes.

The molecular complex comprises a polynucleotide complexed to a carrier which is a conjugate of a cell-specific binding agent and a polynucleotide-binding agent. The cell-specific binding agent is specific for a cellular surface structure, typically a receptor, which mediates internalization of bound ligands by endocytosis, such as the asialoglycoprotein receptor of hepatocytes. The cell-specific binding agent can be a natural or synthetic ligand (for example, a protein, polypeptide, glycoprotein, etc.) or it can be an antibody, or an analogue thereof, which specifically binds a cellular surface structure which then mediates internalization of the bound complex. The polynucleotide-binding component of the conjugate is a compound such as a polycation which stably complexes the polynucleotide under extracellular conditions and releases it under intracellular conditions so that the polynucleotide can function within the cell.

Preferably, the complex of the polynucleotide and the carrier is stable and soluble in physiological fluids. It can be administered in vivo where it is selectively taken up by the target cell via the surface-structure-mediated endocytotic pathway.

Translocation or fusion of endosomes to lysosomes can be inhibited by an agent such as a drug or molecule which inhibits microtubule formation. A preferred agent for inhibiting microtubule formation is colchicine. The method of this invention is useful in gene therapy and in other applications where enhanced expression of a polynucleotide introduced into a cell is desired.

DETAILED DESCRIPTION OF THE INVENTION

Figure 1:
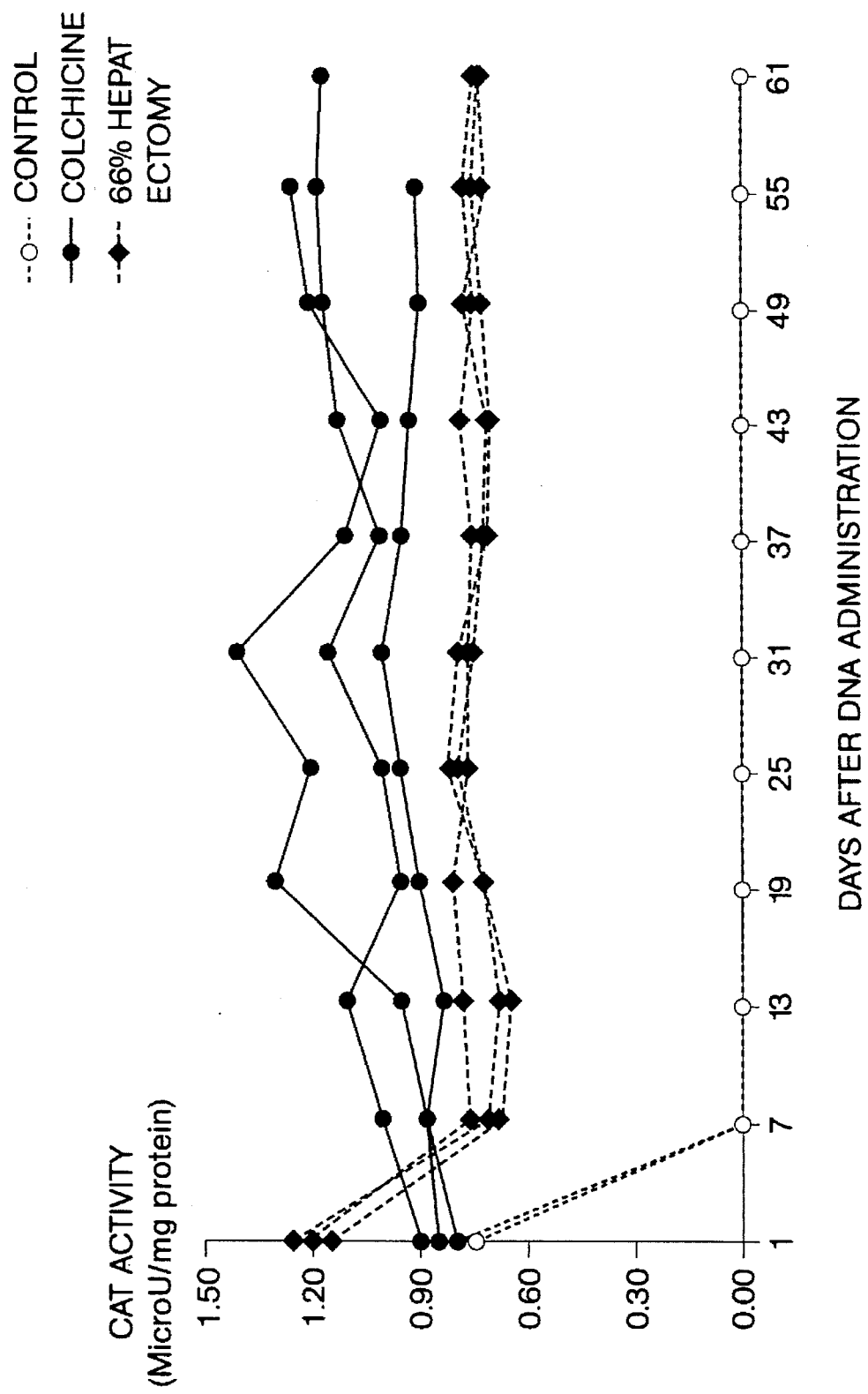
FIG. 1 shows the carrier-DNA complex was infused intravenously 30 minutes after intraperitoneal injection of 0.75 mg/kg colchicine (—●—) or 20 minutes before 66% hepatectomy (—•◆—•). Control rats received an intraperitoneal injection of the vehicle (dimethylsulfoxide) 30 minutes before DNA administration (—•○—•). Rats were sacrificed at time points indicated in the abscissa.

A soluble, targetable molecular complex is used to selectively deliver a gene to a target cell or tissue. An agent is administered in conjunction with the molecular complex to inhibit translocation or fusion of endosomes to lysosomes and decrease degradation of the molecular complex.

The molecular complex comprises the gene to be delivered, complexed to a carrier made up of a binding agent specific for the target cell and a gene-binding agent. The complex is selectively taken up by the target cell and the polynucleotide is incorporated by the cell.

The gene can be DNA, RNA or an analogue thereof. Typically, it comprises a structural gene encoding a desired protein in a form suitable for processing by the target cell. For example, the gene encodes appropriate signal sequences which provide for trafficking to intracellular destinations or cellular secretion of the product. The signal sequence may be the natural sequence of the protein or exogenous sequences. The structural gene is linked to appropriate genetic regulatory elements required for expression of the gene product by the target cell. These include a promoter and, optionally, an enhancer element operable in the target cell. The gene can be contained in an expression vector such as a plasmid or a transposable genetic element along with the genetic regulatory elements necessary for expression of the gene and secretion of the gene-encoded product.

The carrier component of the complex is a conjugate of a cell-specific binding agent and a polynucleotide-binding agent. The cell-specific binding agent specifically binds a cellular surface structure which mediates its internalization into cellular endosomes by, for example, the process of endocytosis. The surface structure can be a protein, polypeptide, carbohydrate, lipid or combination thereof. It is typically a surface receptor which mediates endocytosis of a ligand. Thus, the binding agent can be a natural or synthetic ligand which binds the receptor. The ligand can be a protein, polypeptide, glycoprotein, glycopeptide or glycolipid which has functional groups that are exposed sufficiently to be recognized by the cell surface structure. It can also be a component of a biological organism such as a virus, cells (e.g., mammalian, bacterial, protozoan) or artificial carriers such as liposomes.

The binding agent can also be an antibody, or an analogue of an antibody such as a single chain antibody, which binds the cell surface structure.

Ligands useful in forming the carrier will vary according to the particular cell to be targeted. For targeting hepatocytes, glycoproteins having exposed terminal carbohydrate groups such as asialoglycoprotein (galactose-terminal) can be used, although other ligands such as polypeptide hormones may also be employed. Examples of asialoglycoproteins include asialoorosomucoid, asialofetuin and desialylated vesicular stomatitis virus. Such ligands can be formed by chemical (e.g., sulfuric acid) or enzymatic (e.g., neuraminidase) desialylation of glycoproteins that possess terminal sialic acid and penultimate galactose residues. Alternatively, asialoglycoprotein ligands can be formed by coupling galactose terminal carbohydrates such as lactose or arabinogalactan to non-galactose bearing proteins by reductive lactosamination.

For targeting the molecular complex to other cell surface receptors, other types of ligands can be used, such as mannose for macrophages (lymphoma), mannose 6-phosphate glycoproteins for fibroblasts (fibrosarcoma), intrinsic factor-vitamin B12 and bile acids (See Kramer et al. (1992) *J. Biol. Chem.* 267:18598–18604) for enterocytes and insulin for fat cells. Alternatively, the cell-specific binding agent can be a receptor or a receptor-like molecule, such as an antibody which binds a ligand (e.g., antigen) on the cell surface. Such antibodies can be produced by standard procedures.

The polynucleotide-binding agent complexes the gene to be delivered. Complexation with the gene must be sufficiently stable to prevent significant uncoupling of the polynucleotide extracellularly prior to internalization by the target cell. However, the complex is cleavable under appropriate conditions within the cell so that the polynucleotide is released in functional form. A non-covalent bond based on electrostatic attraction between the polynucleotide-binding agent and the gene provides extracellular stability and is releasable under intracellular conditions.

Preferred polynucleotide-binding agents are polycations. These positively charged materials can bind noncovalently with the negatively charged polynucleotide to form a soluble, targetable molecular complex which is stable extracellularly but releasable intracellularly. Suitable polycations are polylysine, polyarginine, polyornithine, basic proteins such as histones, avidin, protamines and the like. A preferred polycation is polylysine (e.g., ranging from 3,800 to 60,000 daltons). Other noncovalent bonds that can be used to releasably link the polynucleotide include hydrogen bonding, hydrophobic bonding, electrostatic bonding alone or in combination such as, anti-polynucleotide antibodies bound to polynucleotide, and strepavidin or avidin binding polynucleotide containing biotinylated nucleotides.

The carrier can be formed by chemically linking the cell-specific binding agent and the polynucleotide-binding agent. The linkage is typically covalent. A preferred linkage is a peptide bond. This can be formed with a water soluble carbodiimide as described by Jung, G. et al. (1981) *Biochem. Biophys, Res. Commun*, 101:599–606. Alternative linkages are disulfide bond, thioether linkage, or strong noncovalent linkages as in avidin-biotin coupling.

The linkage reaction can be optimized for the particular cell-specific binding agent and polynucleotide-binding agent used to form the carrier. Reaction conditions can be designed to maximize linkage formation but to minimize the formation of aggregates of the carrier components. The optimal ratio of cell-specific binding agent to polynucleotide-binding agent can be determined empirically. When polycations are used, the molar ratio of the components will vary with the size of the polycation and the size of the polynucleotide-binding agent. In general, this ratio ranges from about 10:1 to 1:1. Uncoupled components and aggregates can be separated from the carrier by molecular sieve or ion exchange chromatography (e.g., Aquapore™ cation exchange, Rainin).

In one embodiment, asialoorosomucoid-polylysine conjugate is formed with the crosslinking agent 1-(3-dimethylaminopropyl)-3-ethyl carbodiimide. After dialysis, the conjugate is separated from unconjugated components by preparative acid-urea polyacrylamide gel electrophoresis (pH 4–5). The conjugate can be further purified on the carboxymethyl functionalized column. See U.S. patent application Ser. No. 08/043,008, filed Apr. 5, 1993, entitled "Method for Preparing Conjugates of Receptor-Specific Ligands and Polycationic Polypeptides", attorney's docket number TTI-091 filed on even date herewith, the teachings of which are incorporated by reference herein.

The gene can be complexed to the carrier by a stepwise dialysis procedure. In one embodiment, for use with carriers made of polycations such as polylysine, the dialysis procedure begins with a 2M NaCl dialyzate and ends with a 0.15M solution. The gradually decreasing NaCl concentrations results in binding of the polynucleotide to the carrier. In some instances, particularly when concentrations of the polynucleotide and carrier are low, dialysis may not be necessary; the polynucleotide and carrier are simply mixed and incubated.

The molecular complex can contain more than one copy of the same polynucleotide or one or more different polynucleotides. The molar ratio of polynucleotide to the carrier conjugate can range from about 1:100 to about 1:200, depending upon the type and size of carrier and polynucleotide. The ratio can be determined for the particular carrier and polynucleotide by the gel retardation assay described in U.S. Pat. No. 5,166,320.

For in vitro use cultured cells can be incubated with the molecular complex of this invention in an appropriate medium. It can also be used similarly ex vivo to enhance transfection of cells which have been removed from an organism and will subsequently be returned to the organism.

For in vivo use, the molecular complex of this invention can be administered parenterally. Preferably, it is injected intravenously. The complex is administered in solution in a physiologically acceptable vehicle such as sterile saline.

The target cell is treated with an agent in sufficient amount to inhibit translocation or fusion of endosomes to lysosomes. The agent can be a drug or molecule which blocks the formation of cellular microtubules. Such a drug or molecule can accomplish this by inhibiting the polymerization of tubulin molecules to form microtubules (e.g., colchicine) or by taking up much of the free tubulin in the cell to form microtubules and stabilizing them (e.g., taxol). Other agents include vinblastine, vincristine, and vindesine. For in vivo gene therapy, the agent is preferably administered intravenously prior to the intravenous administration of the complex.

Timing of the administering of the agent in vivo is important to prevent inhibition of the internalization process which is also dependent on function of microtubules. The agent should be administered before the complex, preferably about 30 minutes to one hour before.

The method of this invention can be used in gene therapy to selectively deliver a gene to a target cell in vivo for enhanced and/or prolonged expression. For example, a normal gene can be targeted to a specific cell to correct or alleviate a metabolic or genetic abnormality caused by an inherited or acquired defect in a corresponding endogenous gene. The method can also be used to enhance or prolong expression of genes encoding therapeutic proteins or genes encoding antisense constructs directed against expression of an endogenous or exogenous gene. The enhancement of the foreign gene expression makes practical the periodic, but not too frequent, administration of a gene.

This invention is illustrated further by the following examples.

EXAMPLES

Example 1

An asialoglycoprotein-polycation conjugate consisting of asialoorosomucoid coupled to poly-L-lysine, was used to form a soluble DNA complex capable of specifically targeting hepatocytes via asialoglycoprotein receptors present on these cells. The DNA comprised a plasmid containing the gene for hepatitis B virus surface antigen. Colchicine was used to enhance and prolong gene expression in the target cell.

Expression Vector Containing Gene Encoding Hepatitis B Virus Surface Antigen

Plasmid pSVHBVsurf was obtained from Dr. T. Jake Liang (Massachusetts General Hospital, Boston, Mass.; Liang, T. J. et al. (1993) *J. Clin. Invest.* 91:1241–1246). The plasmid (approximately 3.6 kbp) is a pUC derivative containing the SV40 origin of replication and the open reading frame for hepatitis B surface antigen (as part of a 1984 bp insert) driven by the SV40 promoter. The plasmid was cloned in *E. coli* and purified as described previously (Birnboim, H. C., and Doly, J. (1979) *Nucleic Acids Res.* 7:1513–1518). Purity was checked by electrophoresis through agarose gels stained with ethidium bromide (Maniatis, T., Fritsch, E. F., and Sambrook, G. in Molecular Cloning, A Laboratory Manual, Fritsch, E. G. and Maniatis, T., eds., Cold Spring Harbor Laboratory, Cold Spring Harbor, N.Y. pp 150–161 (1982)).

Asialoorosomucoid

OR was prepared from pooled human serum (Wu, G. Y. and Wu, C. H. (1988) *J. Biol Chem.* 263:14621–14624; Whitehead, D. H. and Sammons, H. G. (1966) *Biochem. Biophys. Acta* 124:209–211) and dissolved in water. An equal volume of 0.2 $NH_2SO_4$ was added to the OR solution and the resulting mixture heated at 80° C. for 1 hour in a water bath to hydrolyse sialic acids from the protein. The acidolysis mixture was removed from water bath, neutralized with NaOH, dialyzed against water for 2 days and then lyophilized. The thiobarbituric acid assay of Warren was then used to verify desialylation of the OR (Warren, L. (1959) *J. Biol. Chem.* 244:1971–1975). Also see generally Warren, L. (1959) *J. Clin. Invest.* 38:755–761 and Schmid, K. et al. (1967) *Biochem. J.* 104:361–368.

The Targetable DNA Carrier

ASOR was coupled to poly-L-lysine (Sigma Chemical Co., St. Louis, Mo.) Mr=41,100 (1:1 molar ratio) at pH 7.4 using 1-ethyl-3-(3-dimethyl-aminopropyl) carbodiimide (Pierce Chemical Co., Rockford, Ill.). The conjugates were purified by cation exchange chromatography using a high pressure liquid chromatographic system (Rainin) employing an Aquapore C-300 column (Rainin) and stepwise elution with 1M urea, 0.1M sodium acetate pH 5.0, 2.5, 2.25, and 2.0. The second peak eluted from the column as detected by U.V. absorption at 230 nm was determined as the optimal conjugate (Jung, G. et al. (1981) *Biochem. Biophys. Res, Commun.* 101:599–606).

The optimal proportion of DNA to mix with the conjugate to form a soluble complex was determined using gel retardation assay as described previously (Wu, G. Y. and Wu, C. H. (1987) *J. Biol. Chem.* 262:4429–4432). Briefly, samples containing equal amounts of DNA in 0.15M NaCl were mixed with increasing amounts of the conjugate in 0.15M NaCl to determine the conjugate to DNA molar ratio which completely retards DNA migration in the gel after filtration through 0.45 micron membranes. The amount of conjugate needed to bind 50–75% of the DNA was calculated and used to form the molecular complex in order to ensure solubility of the complex. To form the soluble molecular complex, the conjugate solution was added very slowly to the DNA by a peristaltic pump at a speed of 0.1 ml/min with constant mixing. An aliquot was taken and absorbance at 260 nm was determined to monitor the amount of DNA. Another aliquot was taken and run on an agarose gel to verify the formation of complex. The solution containing the complex was filtered through a 0.45µ membrane filter. Aliquots were taken for testing by agarose gel electrophoresis as described above.

Timing of Colchicine Administration

Groups of 150 g female rats (Sprague-Dawley), two each, were anesthetized with ketamine-xylazine. Groups of rats were injected intraparenterally with colchicine in sterile phosphate buffered saline, 0.75 mg/kg, one hour prior to, at the time of, and one hour after intravenous (slowly via the tail vein) injection of the complex which contained 2 mg of DNA. A fourth group of rats received only the complex. After 24 hours, the rats were bled and serum was obtained for assay of hepatitis-B virus surface antigen (HBsAg). (Auszyme Monoclonal, EIA Kit for detection of HBV—Abbott). The U. V. absorbance of the resultant solution color change was measured at 492 nm for 200 µl of serum.

Results

In control rats, the mean of HBsAg detected by ELISA on the first day after injection was 0.42±0.72 ng/ml. Treatment with colchicine, one hour prior to, at the time of, or one hour after injection of the DNA complex resulted in mean HBsAg levels of 2.06±3.55 ng/ml, 1.26±1.53 ng/ml and 0.30±0.30 ng/ml, respectively. These data show that treatment with colchicine one hour prior to injection of DNA complex produced the highest levels of gene expression at 24 hours.

To determine the time course of expression of the targeted gene, 4 control rats without colchicine were used for a day 1 time point and 2 for a day 16 time point. For a time course of the effects of colchicine on the duration of expression, 8 rats were used for a day 1 time point and 3 each for day 4 and day 20 points. The results revealed that rats that received complexed DNA only had surface antigen levels of 0.45±0.41 on day 1, but declined to 0.06±0.00 ng/ml on day 16. In contrast, animals pretreated with colchicine 1 hour prior to injection resulted in levels of 2.29±1.20 on day 1, 0.89±0.12 on day 4 and 0.22±0.13 ng/ml on day 20. These data indicate that colchicine not only increases the level of expression early in the time course but also results in longer and higher levels of expression.

Example 2

An ASOR-PL conjugate was used to target a plasmid containing the gene for bilirubin-UDP-glucuronosyl-transferase to hepatocytes of Gunn rats. Colchicine was used to prolong expression.

Animals

Male Sprague-Dawley rats (150–200 g) and bilirubin-UDP-glucuronosyltransferase (B-UGT) deficient Gunn rats (150–225 g) were obtained from a colony at the Albert Einstein College of Medicine. The rats were maintained on standard laboratory rat chow in a 12 hour light/dark cycle.

Colchicine Administration

In experiments to determine the effect of colchicine on hepatic microtubules, colchicine (0.5 mg/ml of dimethylsulfoxide) in doses of 0.25 mg to 1.0 mg per kg was injected intraperitoneally into Sprague-Dawley rats. For gene targeting experiments, 0.75 mg/kg colchicine was used 30 minutes before administration of the carrier-DNA complex (see below).

Plasmids

A plasmid, p(9–12)albCAT, containing the gene for bacterial chloramphenicol acetyltransferase (CAT) driven by an albumin promoter/enhancer was provided by James M. Wilson, University of Pennsylvania, Philadelphia. This plasmid, which was previously shown to express CAT activity after targeted delivery to the liver, in vivo (Wu, G. Y. et al. (1991) *J. Biol. Chem.* 266:14338–14342) was used for determination of the intracellular fate of endocytosed DNA in this study. For transferring B-UGT activity to Gunn rat livers, a plasmid pSVK3-hBUGT$_1$ was used. This construct was produced by cloning the full-length coding region of human liver B-UGT$_1$ (Ritter, J. K. et al. (1991) *J. Biol. Chem.* 266:1043–1047) cDNA downstream to the SV40 promoter region of the pSVK3 backbone (Pharmacia, Uppsala, Sweden). The insert is followed by an SV40 splice site and an SV40 polyadenylation region.

Synthesis of the ASGP-Polylysine Conjugate and Formation of the DNA-Carrier Protein Complex ASOR was prepared as described above. ASOR was covalently linked with polylysine (Sigma, average molecular weight 59000) as previously described (Wu, G. Y. et al. (1991) *J. Biol. Chem.* 266:14338–14342 and Wilson, J. M. et al, (1992) *J. Biol. Chem.* 267:11483–11489). To form targetable carrier-DNA complexes, plasmid DNA, 0.5 mg in 1 ml of 2M NaCl was added to the ASOR-polylysine conjugate (containing 0.15 mg ASOR) in 0.6 ml of 2M NaCl at 25° C. The mixture was placed in a dialysis tubing (1.0 cm flat width) with an exclusion limit of 12000 to 14000 dalton and dialyzed successively at 4° C. for 30 minutes against 1000 ml of each of the following concentrations of NaCl: 1.5M, 1.0M, 0.5M, 0.25M and 0.15M. After the final dialysis, the complex was filtered through 0.45µ membranes for injection into rats.

Administration of the DNA-Carrier Complex and Partial Hepatectomy

Rats were anesthetized with ether and the right external jugular vein was exposed. The soluble complex containing 22 pmol of the DNA in a volume of 0.5 ml, was infused into the right external jugular vein, the vein was ligated and the incision was closed. In one group, 66% hepatectomy was performed through a midline incision (Seglen, P. O. (1976) *Methods Cell Biol,* 13:29–83) under ether anesthesia, 20 minutes after infusion of the DNA-polylysine complex. In preliminary studies, it was determined that 20 minutes was required for maximum internalization of the injected DNA-carrier complex by the liver. Rats in both control and partial hepatectomy group were killed at 20 minutes, 1 hour, 4 hours, 24 hours and 7 days after infusion of the DNA-carrier complex, the livers were removed and subjected to DNA analysis.

Assay of CAT Activity

CAT activity in the liver homogenates was assayed in triplicate using $^{14}$C-chloramphenicol as a substrate and thin-layer chromatographic analysis as previously described (Gorman, C. M. et al. (1982) *Mol. Cell Biol.* 2:1044–1051). The assay was performed in triplicate.

Assay Of B-UGT Activity

B-UGT activity in liver microsomal fractions was determined using UDP-[$^{14}$C] glucuronic acid as substrate (5 mM, 0.2 µCi/µmol) (Jansen, P. L. M. et al. (1977) *J. Biol. Chem.* 252:2710–2716). Blanks contained no bilirubin. Bilirubin and its glucuronides were extracted and separated by thin-layer chromatography (Chowdhury, R. et al. (1979) *J. Biol. Chem.* 254:8336–8339) and detected by autoradiography using authentic bilirubin monoglucuronide and diglucuronide as standard. The silica gel containing the bilirubin monoglucuronide and diglucuronide bands were collected by scraping, the pigments were extracted in methanol and radioactivity was determined after appropriate quench correction.

Analysis of Serum Bilirubin and Pigments Excreted in Bile

Serum bilirubin levels were determined as previously described (Trotman, B. W. et al. (1982) *Anal. Biochem.* 121:175–180). For bile pigment analysis, rats were placed under ether anesthesia and bile ducts were cannulated with PE-10 cannulae. The rats were placed in a restraining cage and allowed to regain consciousness and normal body temperature before collecting bile. Bile was analyzed by high pressure liquid chromatography (Spivak, W. and Carey, M. C. (1985) *Biochem. J.* 225:787–795.

CAT Activity

In the partial hepatectomy and sham operated groups, no CAT activity was detectable in the liver samples at 20 minutes or 4 hours after administration of the plasmid. At 24 hours, CAT activity was detected at approximately 1.0 microunit/mg protein in both sham operated and 66% hepatectomized rats. Seven days after DNA administration, CAT activity was undetectable in sham operated rats but was detected at approximately 1.0.microunit per mg protein in the 66% hepatectomy group. In long-term experiments, CAT activity persisted for at least 60 days (duration of the experiment) (FIG. 1).

In rats that received colchicine, 0.75 mg/kg 30 minutes before the administration of carrier-p(9–12)-albCAT complex, CAT activity persisted in the liver at a level of 1.25 to 1.5 microunits/mg protein for at least 60 days (duration of this study) (FIG. 1).

B-UGT Activity

Control Gunn rat livers had no B-UGT activity. Gunn rats that received carrier-pSK3-hBUGT complex, 30 minutes after the injection of colchicine, B-UGT activity was detected in the liver for up to 6 weeks (last time point of determination). The enzyme activity ranged from 3 to 5% of the activity in the normal Wistar rat liver. In Gunn rats that received the carrier-DNA complex, but no colchicine, hepatic B-UGT activity was detectable only 24 hours after administration of the DNA.

Excretion of Bilirubin Glucuronides in Bile

Control Gunn rat bile contained no detectable bilirubin monoglucuronide or diglucuronide. In three rats that received colchicine followed by the carrier-DNA complex, bile pigments were analyzed at day 5, day 14 and day 60 after DNA administration. In all cases, bilirubin monoglucuronide and diglucuronide were detected in bile. Bilirubin glucuronides accounted for 9 to 15% of total pigment excretion in bile.

Serum Bilirubin Levels

Figure 2:
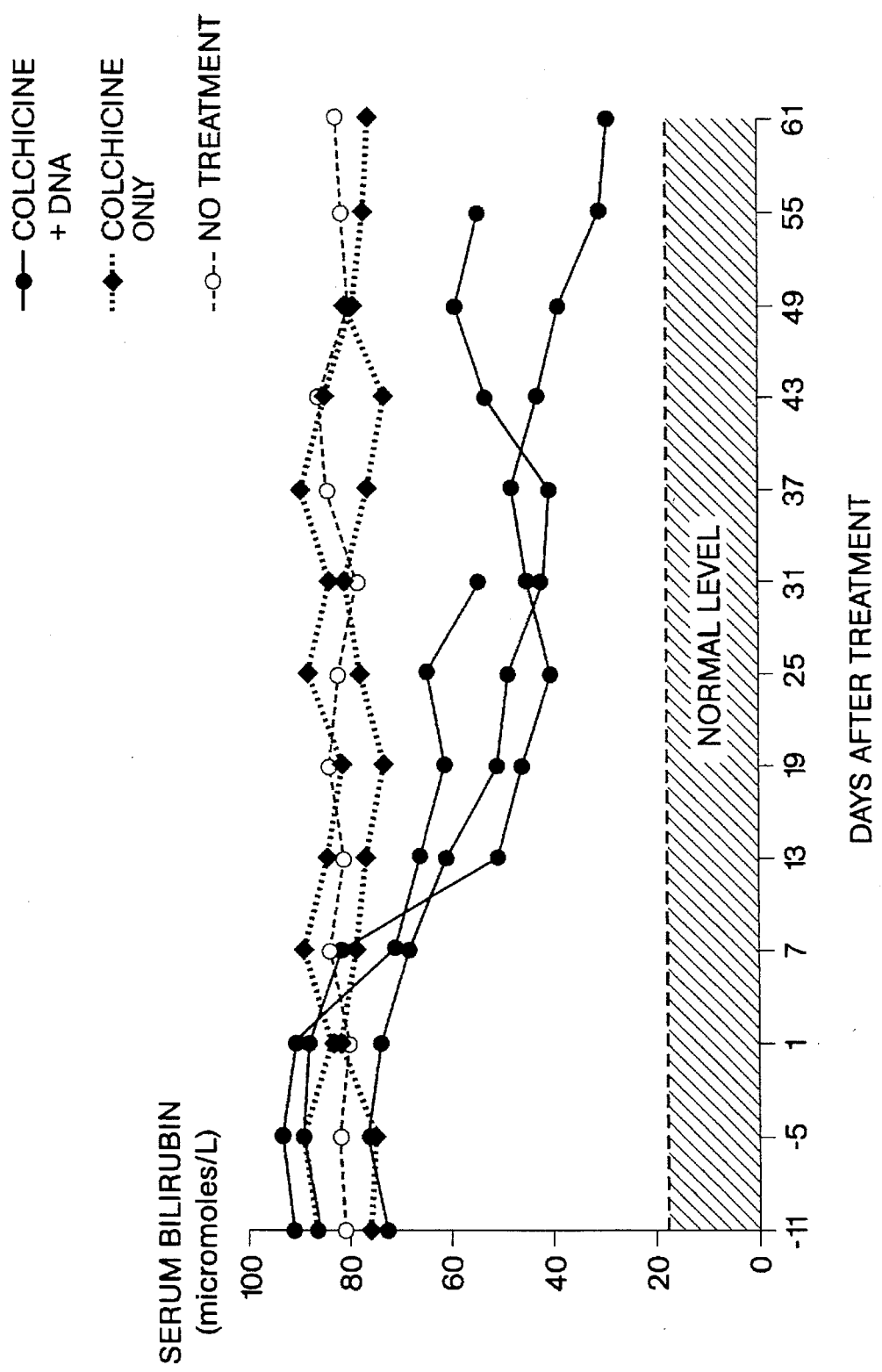
FIG. 2 shows serum bilirubin levels in rats receiving pSV3-hBUGT$_1$, a vector for expression of bilirubin-UDP-glucuronosyltransferase: Gunn rats were injected with colchicine (0.75 mg/kg, intraperitoneally) 30 minutes before infusion of the carrier-DNA complex. Three groups of results are shown: (a) Control rats: no treatment (—•○—•); (b) colchicine only (...◆...); and (c) colchicine followed by DNA targeting (—●—). Blood was collected from tail veins at time points indicated on the abscissa and serum bilirubin level was determined as described in the exemplification.

In untreated Gunn rats and Gunn rats that received colchicine only, there was no significant decrease in serum bilirubin levels (FIG. 2). In rats that received the carrier-pSK3-hBUGT complex, but no colchicine, there was also no significant decrease in serum bilirubin levels. In contrast, when the carrier-DNA complex was administered 30 minutes after the injection of colchicine, 0.75 mg/kg, serum bilirubin concentration declined progressively for at least 5 weeks to 45% of the pretreatment level. After this period the bilirubin level gradually increased to 70% of the pretreatment level in 60 days. In another rat, the serum bilirubin level decreased to 30% of the pretreatment level in 35 days and remained at that level for at least 60 days (duration of this experiment).

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

We claim:

1. A method of inhibiting degradation of a polynucleotide following internalization of the polynucleotide by a cell in a mammal, the method comprising the steps of sequentially administering to the mammal:
   (a) colchicine in an amount sufficient to inhibit formation of microtubules in the cell and to inhibit degradation of a subsequently administered polynucleotide; and
   (b) a molecular complex targeted for specific incorporation into the cell, the molecular complex comprising a polynucleotide noncovalently linked to a conjugate of a polycation and a cell-specific binding agent which binds a surface molecule of the cell and is internalized into an endosome of the cell.

2. A method of claim 1 wherein the polynucleotide is DNA.

3. A method of claim 1 wherein the polynucleotide comprises a gene.

4. A method of claim 1 wherein the mammal is a human.

5. A method of claim 1 wherein the polycation is polylysine.

6. A method of claim 1 wherein the cell-specific binding agent is a ligand for the asialoglycoprotein receptor.

7. A method of claim 6 wherein the ligand is a glycoprotein having an exposed terminal carbohydrate group which is recognized by the asialoglycoprotein receptor.

8. A method of claim 1 wherein the cell-specific binding agent is an asialoglycoprotein.

9. A method of inhibiting degradation of a polynucleotide following internalization of the polynucleotide by an hepatocyte in a mammal, the method comprising the steps of sequentially administering to the mammal:
   (a) colchicine in an amount sufficient to inhibit formation of microtubules in the hepatocyte and to inhibit degradation of a subsequently administered polynucleotide; and
   (b) a molecular complex targeted for specific incorporation into an hepatocyte, the molecular complex comprising a polynucleotide noncovalently linked to a conjugate of a polycation and a ligand for the asialoglycoprotein receptor that is internalized into an endosome of the hepatocyte.

10. A method of claim 9 wherein the ligand for the asialoglycoprotein receptor is an asialoglycoprotein.

11. A method of claim 9 wherein the ligand for the asialoglycoprotein receptor is a glycoprotein having an exposed terminal carbohydrate group.

12. A method of claim 9 wherein the polycation is polylysine.

* * * * *